United States Patent [19]

Tang

[11] Patent Number: 4,526,726
[45] Date of Patent: Jul. 2, 1985

[54] TERTIARYALKYL PEROXYCARBONATES

[75] Inventor: Robert H. Tang, Norton, Ohio

[73] Assignee: PPG Industries, Inc., Pittsburgh, Pa.

[21] Appl. No.: 430,051

[22] Filed: Sep. 30, 1982

[51] Int. Cl.$^3$ .......................................... C07C 179/18
[52] U.S. Cl. ..................................... 260/463; 264/83; 525/474; 526/230.5
[58] Field of Search ....................... 260/463, 453 RZ

[56] References Cited

U.S. PATENT DOCUMENTS

| | | | |
|---|---|---|---|
| 2,307,679 | 1/1943 | Hechenbleikner | 260/464 |
| 2,370,588 | 2/1945 | Strain | 260/453 R |
| 2,374,789 | 5/1945 | Strain | 260/463 |
| 2,517,964 | 8/1950 | Bissinger | 260/453 R |
| 2,787,631 | 4/1957 | Stevens | 260/463 |
| 2,820,809 | 1/1958 | Frevel et al. | 260/463 |
| 2,865,904 | 12/1958 | Seed et al. | 526/209 |
| 3,313,762 | 4/1967 | Pfeifer | 524/588 |
| 3,326,859 | 6/1967 | Seiner | 260/453 RZ X |
| 3,627,799 | 12/1971 | Young et al. | 260/463 |
| 3,637,633 | 1/1972 | Dixon | 526/228 |
| 3,849,468 | 11/1974 | Busseret | 260/463 |
| 4,061,704 | 12/1977 | Barter | 264/83 |

FOREIGN PATENT DOCUMENTS

| | | |
|---|---|---|
| 2021327 | 11/1971 | Fed. Rep. of Germany . |
| 2087973 | 2/1972 | France . |
| 46-15086 | 4/1971 | Japan . |

OTHER PUBLICATIONS

Kirillov, Chem. Abstract, vol. 77, 33973n, (1972).
"Esters of Peroxycarbonic Acids", by F. Strain et al., J. Am. Chem. Soc. 72, pp. 1254 et seq., 1950.
"α-Alkoxycarbonylisopropyl Chloroformates and the Peroxydicarbonates Based on Them", by A. I. Kirillov et al., Zhurnal Organicheskoi Khimii, vol. 7, No. 9, pp. 1875–1878, Sep. 1971.
"Di(α-Alkoxycarbonyl)-Isopropyl Peroxydicarbonates as Vinyl Chloride Polymerization Initiators", by A. I. Kirillov et al., Vysokomolekulyarnye Soedineniya Seriya B, (1974), 16, (10).
"Fungicidal N-(3,5-dihalophenyl)Carbamates", F. Akira et al., CA 76:59186n, (1972), Ger. Offen. No. 2,021,327.
"N-Phenylcarbamates," CA 77:88111k, (1972), Fr. Demande 2087973.
"Bis(α,α'-carbalkoxyisopropyl)peroxydicarbonates", by A. I. Kirillov, CA 77:33973n, (1972), U.S.S.R., 335,235.
"α-Cyanoisopropyl Ester of Chloroacetic Acid", by V. P. Kondratenko, et al., CA 65:16871d, (1966), U.S.S.R., 182,134.

Primary Examiner—Diana G. Rivers
Attorney, Agent, or Firm—Irwin M. Stein

[57] ABSTRACT

Described are organic peroxycarbonates of the graphic formula:

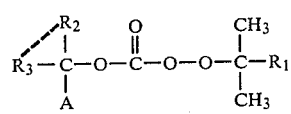

in which $R_1$ is a $C_1$–$C_{14}$ alkyl, phenyl or benzyl group, $R_2$ and $R_3$ are each selected from the group $C_1$–$C_4$ alkyl, $C_5$–$C_7$ cycloalkyl, $C_1$–$C_4$ alkyl substituted $C_5$–$C_7$ cycloalkyl or participate in a cycloalkyl group of from 5 to 7 carbon atoms, provided that when one of $R_2$ and $R_3$ is a cycloalkyl group, the other is an alkyl group, A is cyano or alkoxycarbonyl, i.e.,

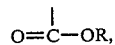

wherein R is a $C_1$–$C_8$ alkyl or cyclohexyl group. Preferably $R_2$ and $R_3$ are each a $C_1$–$C_2$ alkyl group or participate to form a cyclohexyl group, $R_1$ is a $C_1$–$C_3$ alkyl or phenyl and R is a $C_1$–$C_4$ alkyl.

The compounds can be used as initiators for the polymerization and copolymerization of ethylenically unsaturated monomers. The compounds also find application in connection with the curing of polyester resins and the vulcanization of silicone rubbers, e.g., hot air vulcanization.

4 Claims, No Drawings

TERTIARYALKYL PEROXYCARBONATES

DESCRIPTION OF THE INVENTION

Among the primary uses of peroxides is the initiation of the polymerization or copolymerization of ethylenically unsaturated monomers. Other principal uses of peroxides are the curing of unsaturated polyester resins and the vulcanization of rubbers. Peroxides such as peroxycarbonate esters have been used for the vulcanization of silicone rubbers, e.g., the hot air vulcanization of silicone rubbers.

Organic peroxides reported to be useful for silicone rubber vulcanizations include: 2,4-dichlorobenzoyl peroxide, benzoyl peroxide, dicumyl peroxide, tertiarybutyl perbenzoate, ditertiarybutyl peroxide, 2,5-dimethyl-2,5-di(t-butylperoxy)hexane, tertiarybutylperoxy isopropylcarbonate and tertiarybutylperoxy alkylcarbonates in which the alkyl group has from 8 to 26 carbon atoms. Each of the aforesaid initiators has particular advantages and limitations depending on the vulcanizing method used, the nature of the vulcanizable composition and the properties desired in the vulcanizate.

Continuous hot air vulcanization is the most convenient method of vulcanizing extruded silicone rubber articles such as oven seals, tubing and electrical insulation. Until now, 2,4-dichlorobenzoyl peroxide has been the recommended initiator for general use in this process. Benzoyl peroxide is not generally recommended because it tends to produce porous vulcanizates when the rubber compound is heated without external pressure. Dicumyl peroxide can be used in rubbers containing carbon black filler, but its performance is not as good as that of 2,4-dichlorobenzoyl peroxide. It is used preferably in low concentrations to produce rubbers with the low compression set desirable is gaskets and seals; but, at low concentrations, it may leave a skin of tacky, incompletely vulcanized rubber composition on extrudate surfaces exposed to air or steam during vulcanization. Other initiators, such as tertiarybutylperoxy isopropylcarbonate can leave an uncured skin that can be easily removed.

Tertiarybutylperoxy isopropylcarbonate can be used with all types of fillers used in silicone rubber articles. Moreover, it is much less sensitive to friction, mechanical or thermal shock than 2,4-dichlorobenzoyl peroxide. However, it has a relatively low flash point and therefore suffers from the disadvantage of being relatively volatile during hot air vulcanization.

U.S. Pat. No. 2,374,789 discloses alkylperoxy alkylcarbonates as polymerization catalysts for ethylenically unsaturated compounds. Among the peroxycarbonate compounds disclosed therein is tertiarybutylperoxy isopropylcarbonate, which also has been reported in the chemical literature, e.g., Journal of the American Chemical Society, Volume 72, page 1259 (1950).

U.S. Pat. No. 3,313,762 describes the use of tertiaryalkylperoxy alkylcarbonates as a curing agent for the preparation of molded organopolysiloxane elastomers. These peroxycarbonates are reported to produce vulcanizates with superior toughness, resistance to change in physical properties from heat aging, and with a low degree of compression set. The alkyl groups of these peroxycarbonates have up to 8 carbon atoms.

U.S. Pat. No. 4,061,704 describes tertiaryalkylperoxy alkylcarbonate initiators in which the tertiaryalkyl group has from 4 to 14 carbon atoms and the O-alkyl portion of the initiator contains from 8 to 26 carbon atoms. These peroxycarbonates are described as useful curing agents for the hot air vulcanization of silicone rubber compounds, as well as in mold and other vulcanization methods, to provide vulcanizates having low porosity, no objectionable odor, and a smooth, firm, completely cured surface.

Japanese Pat. No. 46-15086 describes the synthesis of tertiaryalkylperoxy alkylcarbonates with O-alkyl groups containing 8 to 16 carbon atoms. These peroxycarbonates are reported to be useful as polymerization initiators for monomers such as ethylene and styrene, and as cross-linking agents for polyethylenes, ethylene-propylene copolymers, and ethylene-vinyl acetate copolymers.

The present invention relates to a group of novel tertiaryalkylperoxy alkoxycarbonyl alkyl or cycloalkyl carbonates and tertiary alkylperoxy cyanoalkyl carbonates which can be employed as initiators in the hot air vulcanization of silicone rubber compounds, as well as in mold and other vulcanization methods to provide silicone rubber vulcanizates. These organic peroxycarbonates are also provided for use as initiators for the polymerization or copolymerization of ethylenically unsaturated monomers and for the cross linking of unsaturated polyester resins.

DETAILED DESCRIPTION OF THE INVENTION

The novel organic peroxycarbonates of the present invention can be represented by the graphic formula:

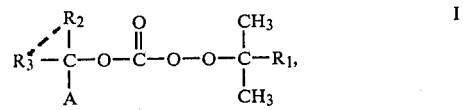

wherein $R_1$ is a $C_1$-$C_{14}$ alkyl, phenyl or benzyl group, $R_2$ and $R_3$ are each selected from the group consisting of $C_1$-$C_4$ alkyl, $C_5$-$C_7$ cycloalkyl, $C_1$-$C_4$ alkyl substituted $C_5$-$C_7$ cycloalkyl, or participate in a cycloalkyl group of from 5 to 7 carbon atoms (as shown by the broken line connecting $R_2$ and $R_3$), provided that when one of $R_2$ and $R_3$ is a cycloalkyl group, the other is $C_1$-$C_4$ alkyl group, and A is cyano or alkoxycarbonyl.

More particularly, the organic peroxycarbonates of the present invention can be represented by the graphic formulae:

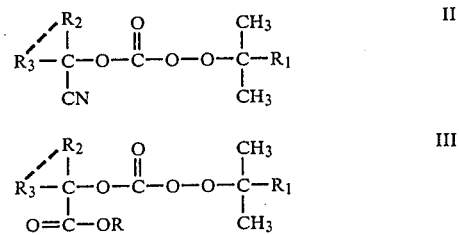

wherein $R_1$, $R_2$, and $R_3$ are as defined above, and R is a $C_1$-$C_8$ alkyl or cyclohexyl group. Preferably, $R_2$ and $R_3$ are each a $C_1$-$C_2$ alkyl group or together participate to form a cyclohexyl group, $R_1$ is a $C_1$-$C_8$ more preferably a $C_1$-$C_3$, alkyl or phenyl group, and R is a $C_1$-$C_4$ alkyl.

The alkyl groups of R, $R_1$, $R_2$ and $R_3$ are preferably simple alkyl groups, i.e., straight or branched open-chain, saturated, unsubstituted alkyl groups such as methyl, ethyl, isopropyl, n-butyl, secondary butyl, tertiarybutyl, amyl, hexyl, heptyl, octyl, 2-ethylhexyl, decyl, undecyl dodecyl, tridecyl and tetradecyl.

Specific examples of the organic peroxycarbonates of the present invention include but are not limited to: tertiarybutylperoxy-α-methoxycarbonyl isopropylcarbonate(tertiarybutylperoxy-1-methylcarboxylate-1-methylethylcarbonate), tertiarybutylperoxy-α-ethoxycarbonyl isopropylcarbonate, tertiarybutylperoxy-α-isopropoxycarbonyl isopropylcarbonate, tertiarybutylperoxy-α-cyclohexoxycarbonyl isopropylcarbonate, tertiaryamylperoxy-α-methoxycarbonyl isopropylcarbonate, α-cumylperoxy-α-methoxycarbonyl isopropylcarbonate, tertiarybutylperoxy-α-secondarybutoxycarbonyl isopropylcarbonate, tertiarybutylperoxy-α-n-propoxycarbonyl isopropylcarbonate, and tertiarybutylperoxy-α-2-ethylhexoxycarbonyl isopropylcarbonate, tertiarybutylperoxy-1-cyano-1-methylethylcarbonate, tertiarybutylperoxy-1-cyano-1-cyclohexylcarbonate, and tertiarybutylperoxy-1-cyano-1-cyclohexylethylcarbonate.

The organic peroxycarbonates of the present invention can be prepared by reacting the corresponding tertiary alkyl hydroperoxide with the corresponding alpha-alkoxycarbonyl alkyl or cycloalkyl chloroformate or dialkyl cyanohydrin chloroformate in the presence of an alkaline reagent, i.e., an organic or inorganic base such as sodium hydroxide, at temperatures preferably below 20° C. See, for example U.S. Pat. No. 2,374,789 and Strain et al, Esters of Peroxycarbonic Acids, Journal of the American Chemical Society, Vol. 72, page 1254 (1950), where the reaction of an alkyl hydroperoxide and alkyl chloroformate is described.

The tertiaryalkyl hydroperoxides, alpha-alkoxycarbonyl alkyl (or cycloalkyl) chloroformates, and dialkyl cyanohydrin chloroformates used to prepare the peroxycarbonates of the present invention can be represented by the graphic formulae:

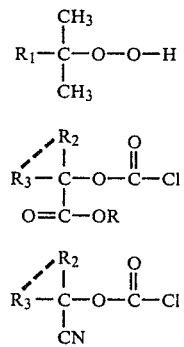

wherein R, $R_1$, $R_2$ and $R_3$ are as defined above with respect to graphic formulas II and III.

Tertiaryalkyl hydroperoxides are typically derived from the corresponding tertiaryalkyl alcohols, i.e., $R_1$—C(CH$_3$)$_2$—OH by known methods. The alpha-alkoxycarbonyl alkyl chloroformate of formula IV can be obtained by the reaction of the corresponding alpha-hydroxyalkanoic acid ester with phosgene in a manner well known in the art. For example, alpha-hydroxyisobutyric acid can be obtained by the oxidation of isobutylene with nitrogen tetroxide, and the ester of that acid can be obtained by reacting it with an alcohol having the formula, R—OH, wherein R is the same as defined above with respect to graphic formula III. The chloroformate of the dialkyl cyanohydrin can be prepared by the reaction of the corresponding cyanohydrin with phosgene using well known phosgenation techniques. The cyanohydrin in turn can be prepared by the reaction of the corresponding ketone with hydrocyanic acid at temperatures of from 10° C. to 20° C. using well known techniques such as described for the preparation of acetone cyanohydrin in Organic Synthesis, Vol. II, pp. 7–8, John Wiley and Sons, New York, A. H. Blatt, Ed., 1943.

The preparation of alpha-alkoxycarbonyl isopropyl chloroformates and peroxydicarbonates based thereon are described in Zhurnal Organicheskoi Khimii, Volume 7, No. 9, pages 1875–1878, September, 1971. The use of such peroxydicarbonates as polymerization initiators for vinyl chloride is described in Vysokomolekulyarnye Soedineniya Seriya B (1974) 16 (10).

In accordance with an embodiment of the present invention, silicone rubber is prepared by heating a composition comprising a mixture of an organopolysiloxane polymer that is curable to an elastomeric state and one or more of the hereinbefore described tertiaryalkylperoxy carbonate cure initiators. Usually a reinforcing filler such as precipitated silica or carbon black is added, but a semi-reinforcing filler such as a clay or diatomaceous earth can be used if desired.

Useful organopolysiloxane, or silicone polymers include all of those known in the art which are curable to an elastomeric state. Silicone polymers may be represented by the formula:

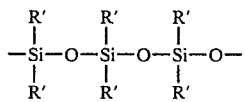

where each R' independently is an organic side group selected from monovalent hydrocarbon and halogenated hydrocarbon groups and cyanoalkyl groups. The proportion of the number of side groups R' to the number of silicon atoms may vary slightly depending on polymer length, the nature of chain-end groups, degree of crosslinking, etc. Generally, the ratio is in the range of from about 1.95 to about 2.01, preferably from about 1.98 to about 2.01. These silicone polymers are prepared by the condensation polymerization of low molecular weight organopolysiloxane oils. Catalysts for the condensation include ferric chloride hexahydrate, phenyl phosphoryl chloride, potassium hydroxide, sodium hydroxide, and others. The polymers are generally in the form of a very viscous mass or a gum.

The low molecular weight organopolysiloxane oils are made by the hydrolysis and dehydration of corresponding dihalosilanes and trihalosilanes, R'SiCl$_2$ are R'SiCl$_3$, where R' has the same definition as for the polymer. The hydrolysis is done at low temperature, about 0° C. or lower, for example in ice water. A solvent or diluent such as butanol or ethyl ether may be present. The halosilane may be diluted with a solvent such as ether or toluene prior to hydrolysis. Hydrolysis produces a diorganodihydroxysilane which dehydrates to give the low molecular weight silicone oils. Addition of trihalosilane in the hydrolysis reaction gives a low molecular weight cross-linked product which is polymerizable to a hard resin.

U.S. Pat. Nos. 2,541,137, 2,448,556, 2,448,756, 2,521,528, 2,457,688, and 3,313,762 describe silicone polymers which may be used with the tertiaryalkylperoxy carbonate cure initiators of this invention.

Organopolysiloxane copolymers containing alkenyl side groups are preferred. The groups may be vinyl, allyl, etc. Usually they are vinyl groups. The vinyl side groups are typically a small proportion of the total number of side groups, preferably from about 0.05 to about 2 mole percent. The presence of unsaturated groups in the polymer does not lead to ozone degradation of the vulcanizate, as might be expected, because the groups become saturated in the course of vulcanization. One copolymer of this type is easily prepared by hydrolyzing and then polymerizing a mixture of dimethyldichlorosilane and methylvinyldichlorosilane having the desired proportion of vinyl groups.

The quantity of tertiaryalkylperoxy carbonate to be used can vary widely, depending on the nature of the rubber composition and the chosen method of vulcanization. It should be a minor amount sufficient to cure the composition to an elastomeric state. Generally from about 0.1 to about 10 parts, often from about 0.1 to about 5 parts, usually from about 0.25 to about 3 parts, of initator per 100 parts of silicone polymer may be used.

In a method of vulcanization, such as hot air vulcanization, where incomplete surface cure can be a problem, the peroxycarbonates of the present invention will be used in minor amounts, i.e., less than about 10 parts, sufficient to provide complete surface cure, as indicated by the absence of tacky, uncured rubber composition on the surface of the vulcanizate. The amount necessary for good hot air vulcanization depends in part on the particular initiator being used, on the vulcanization temperature, the residence time, the type of silicone polymer, the kind and amount of filler, etc., but will fall generally within the ranges specified above.

Other organic peroxide initiators such as dicumyl peroxide and tertiary-butyl perbenzoate may be used in combination with the tertiary-alkylperoxy carbonates of the present invention in order to impart special properties to the vulcanizate.

Any of the commonly used reinforcing and semi-reinforcing fillers may be used. Reinforcing fillers include carbon black and the manufactured silicas. The manufactured silicas, which provide the greatest degree of reinforcement, include fumed silica, made by burning silicon tetrachloride or ethyl silicate in the vapor phase, and precipitated silica, made by precipitation of a soluble silicate, as described, for example, in U.S. Pat. No. 2,940,830. A typical commercial form of reinforcing precipitated silica is manufactured and sold by PPG INDUSTRIES, INC., under the designation Hi-Sil 233. Semi-reinforcing fillers include diatomaceous earth, lithopane, calcium carbonate, and metal oxides such as titanium oxide and iron oxide.

Other conventional ingredients may be present: heat stabilizers such as red iron oxide or aryl urethanes; blowing agents; process aids to ease the milling of compositions with high filler content; pigments, preferably inorganic; and structure additives such as silanol-stopped and alkoxy-stopped polydiorganosiloxanes, for examples, polydimethylsiloxanes, and diphenylsilanediol.

The various ingredients of the composition may be mixed in any conventional way, for example on a roll mill or in a Banbury or a dough-mixer. The order of addition of the ingredients is not critical, but it is preferable to add the cure initiator to the silicone polymer when the filler is added or afterward. After mixing, the vulcanizable composition is shaped to form an article that is then vulcanized by heating.

The composition can be vulcanized by all of the common methods. For example, it can be molded under heat and pressure, generally from about 100° to 300° C. or higher and from about 100 to about 2000 p.s.i. or more for an appropriate time. Hot liquid vulcanization can be used, wherein the composition is passed through a bath of heated liquid. Although autoclave vulcanization sometimes gives incomplete surface cures unless the article to be vulcanized is wrapped in cellophane or damp cloth, compositions containing the initiators of the present invention would not require such a wrapping step.

In hot air vulcanization, the silicone composition, usually in the form of an extruded article, is passed, usually continuously, through a horizontal or vertical chamber such as a hot air oven and contacted directly with heated gas, usually either hot air or steam. The curing temperature is high, typically from about 315° to about 425° C., and residence times, during which the extrudate is heated, are short, from just a second or so up to a minute or more depending on the thickness of the section and on the nature of the composition. The extruded article may be heated for from about 1 to about 120 seconds or more, but a range of from about 30 to about 90 seconds is more usual. For a thin extrusion, the vulcanizing time is typically from about 40 to about 80 seconds.

A post-vulcanization cure in an air circulting oven is generally used to remove vulcanization by-products and low molecular weight polymers, thereby improving the stability and chemical resistance and minimizing the compression set of the vulcanizate. Oven cures of from 1 to 24 hours or more at temperatures up to about 260° C. or higher are typical.

The peroxycarbonate initiators of the present invention can be used to initiate the polymerization or copolymerization of ethylenically unsaturated monomeric compounds, i.e., materials containing the polymerizable group, —CH=CH—, e.g., $CH_2$=CH—. Illustrative of ethylenically unsaturated compounds include: vinyl aromatic compounds, e.g., styrene, p-chlorostyrene; esters of aliphatic alpha-methylene mono carbonic acids, e.g., methylacrylate, n-butyl acrylate, and ethylacrylate; vinyl esters, e.g., vinyl acetate; vinyl halides, e.g., vinyl chloride; vinyl ethers, e.g., vinyl methylethers; vinylidene halides, e.g., vinylidene chloride; and alpha-ethylenically unsaturated hydrocarbons such as ethylene, and propylene.

The amount of peroxycarbonate initiator used can vary; but commonly will range from about 0.003–0.300 weight percent, more usually, from about 0.01–0.20 weight percent, based on the amount of monomer used. Polymerization temperatures will typically be from about 30° C. to about 80° C., more usually from about 55° C. to 65° C.

The peroxycarbonate initiators of the present invention can be used for curing unsaturated polyester resin compositions. Such compositions are well known to those skilled in the art. The amount of peroxycarbonate used for such purpose typically varies from about 0.05 to about 5 parts by weight per 100 weight parts of the unsaturated polyester composition. Cure temperatures vary from about 20° C. to about 100° C.

The present invention is more particularly described in the following example which is intended as illustrative only since numerous modifications and variations therein will be apparent to those skilled in the art.

EXAMPLE 1-(ethyl carboxylate)-1-methylethyl chloroformate was prepared by phosgenation of ethyl-2-hydroxyisobutyrate in ether using pyridine as the acid acceptor. The reaction product was 90% chloroformate 50 grams (0.23 mole) of the 90% chloroformate product, 26 grams (0.26 mole) of 90% t-butyl hydroperoxide and 7.5 grams of 2-propanol were added to a 500 milliliter (ml) round bottom reactor flask. The reaction mixture was agitated and cooled to about 10° C. A solution of 30% sodium hydroxide (37.4 grams, 0.26 mole) was then added slowly to the reaction flask. The reaction mixture was post stirred for 90 minutes following addition of the sodium hydroxide. The organic layer was separated, washed twice with water and dried with anhydrous magnesium sulfate. The dried product (52 grams) was a colorless liquid having a percarbonate assay of 96% by Iodometric titration. Identification of the product as t-butylperoxy(1-ethyl carboxylate)-1-methylethyl carbonate was confirmed by infrared and nuclear magnetic resonance spectroscopy.

Although the present invention has been described with reference to certain details of specific embodiments, it not intended that the invention be construed as limited to the details except insofar as they are set forth in the appended claims.

What is claimed is:

1. An organic peroxycarbonate of the graphic formula:

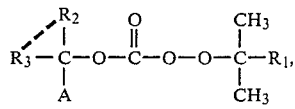

wherein $R_1$ is a $C_1$–$C_{14}$ alkyl, phenyl or benzyl, $R_2$ and $R_3$ are each selected from the group consisting of $C_1$–$C_4$ alkyl, $C_5$–$C_7$ cycloalkyl, $C_1$–$C_4$ alkyl substituted $C_5$–$C_7$ cycloalkyl, or participate in a cycloalkyl group of from 5 to 7 carbon atoms, provided that when one of $R_2$ and $R_3$ is a cycloalkyl group, the other is a $C_1$–$C_4$ alkyl, A is a cyano group.

2. The organic peroxycarbonate of claim 1 wherein $R_1$ is a $C_1$–$C_3$ alkyl or phenyl, $R_2$ and $R_3$ are each a $C_1$–$C_2$ alkyl group or participate to form a cyclohexyl group, and A is cyano.

3. Tertiarybutylperoxy-1-cyano-1-methylethylcarbonate.

4. Tertiarybutylperoxy-1-cyano-1-cyclohexylcarbonate.

* * * * *